(12) United States Patent
Mukaide et al.

(10) Patent No.: US 8,214,158 B2
(45) Date of Patent: Jul. 3, 2012

(54) X-RAY IMAGING APPARATUS, X-RAY IMAGING METHOD AND METHOD OF CONTROLLING X-RAY IMAGING APPARATUS

(75) Inventors: Taihei Mukaide, Atsugi (JP); Kazuhiro Takada, Kawasaki (JP); Masatoshi Watanabe, Isehara (JP)

(73) Assignee: Canon Kabushiki Kaisha, Tokyo (JP)

( * ) Notice: Subject to any disclaimer, the term of this patent is extended or adjusted under 35 U.S.C. 154(b) by 412 days.

(21) Appl. No.: 12/526,418

(22) PCT Filed: Mar. 11, 2009

(86) PCT No.: PCT/JP2009/055215
§ 371 (c)(1), (2), (4) Date: Aug. 7, 2009

(87) PCT Pub. No.: WO2009/113713
PCT Pub. Date: Sep. 17, 2009

(65) Prior Publication Data
US 2010/0318302 A1   Dec. 16, 2010

(30) Foreign Application Priority Data
Mar. 12, 2008 (JP) .................................. 2008-062788

(51) Int. Cl.
*G01N 31/00* (2006.01)
(52) U.S. Cl. .......................... 702/28; 702/172; 702/189
(58) Field of Classification Search .................... 702/28, 702/172, 189; 382/132; 378/53, 62, 210
See application file for complete search history.

(56) References Cited

U.S. PATENT DOCUMENTS
5,835,561 A * 11/1998 Moorman et al. ............... 378/98
2008/0080670 A1 * 4/2008 Harding .......................... 378/53

FOREIGN PATENT DOCUMENTS
JP   2007-82663   4/2007

OTHER PUBLICATIONS

T Takeda, "Phase-Contrast and Fluorescent X-Ray Imaging for Biomedical Researches", *Nuclear Instruments and Methods in Physics Research, Section—A:Accelerators, Spectrometers, Detectors and Associated Equipment*, Elsevier, Amsterdam, NL, vol. 548, No. 1-2, Aug. 11, 2005, pp. 38-46, XP025294578.

(Continued)

*Primary Examiner* — Mohamed Charioui
*Assistant Examiner* — Elias Desta
(74) *Attorney, Agent, or Firm* — Fitzpatrick, Cella, Harper & Scinto

(57) ABSTRACT

A simplified X-ray imaging apparatus is capable of computationally determining effective atomic numbers with small error factors even for light elements. In one embodiment, the X-ray imaging apparatus has an X-ray generation unit 101 (400) for generating X-rays and a detector 105 (405) for detecting X-rays transmitted through an object of examination 104 (403). A computing unit 106 (406) computationally determines a quantity of an X-ray phase attributable to the object of examination and an X-ray transmittance of the object of examination from data detected by the detector. The computing unit also computationally determines an effective atomic number of the object of examination from $\rho_e t$ determined from the quantity of the X-ray phase and $\mu t$ determined from the X-ray transmittance.

20 Claims, 7 Drawing Sheets

OTHER PUBLICATIONS

J Baruchel et al., "Phase-Contrast Imaging of Thin Biomaterials", *Biomaterials*, Elsevier Science Publishers BV., Barking, GB, vol. 22, No. 12, Jun. 15, 2001, pp. 1515-1520, XP004245886.

DF Jackson et al., "X-Ray Attenuation Coefficients of Elements and Mixtures", *Physics Reports* (Review Section of Physics Letters) 70, No. 3 (1981) pp. 169-233, North Holland Publishing Company.

Y Ohno et al., "Dual-Energy X-Ray CT with CdTe Array and Its Extension", Elsevier Science Publishers BV., *Nuclear Instruments and Methods in Physics Research, A* 548 (2005) pp. 72-77.

\* cited by examiner

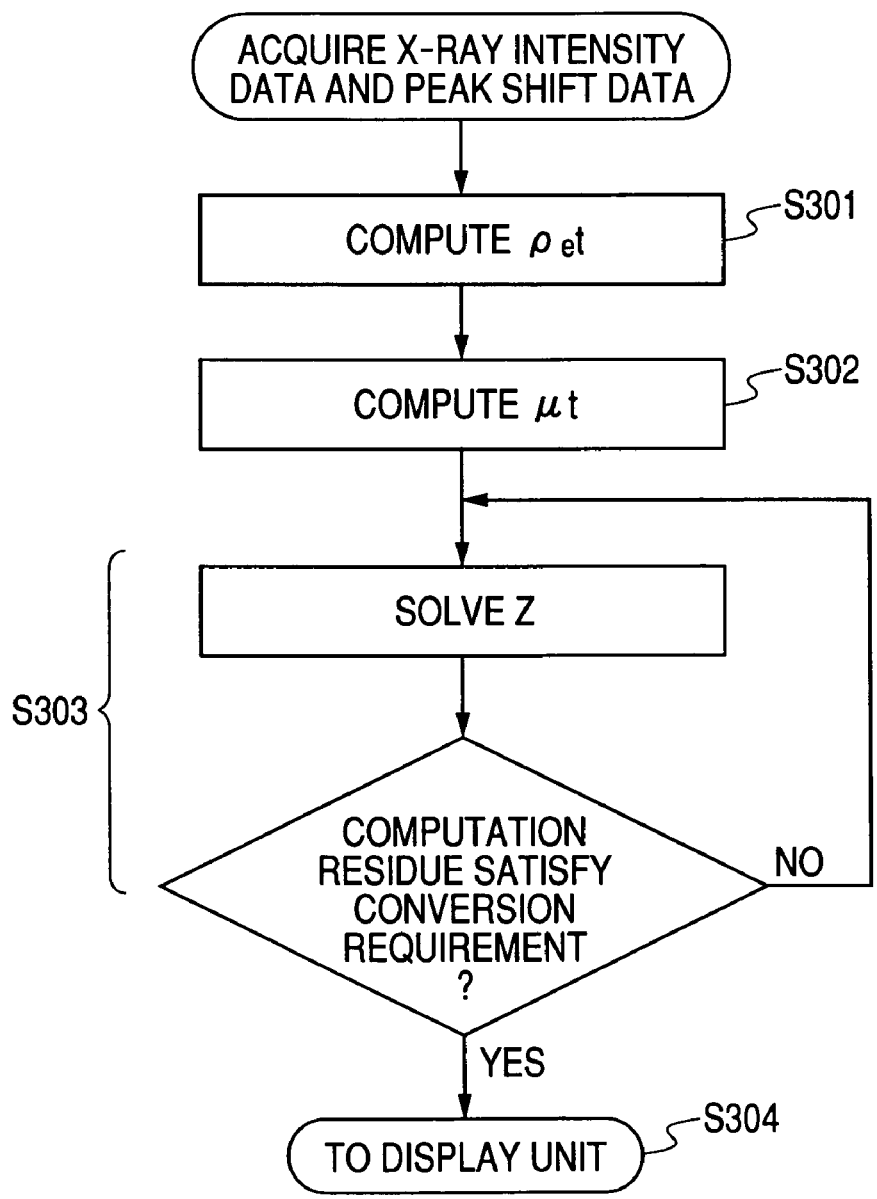

X-RAY IMAGING APPARATUS, X-RAY IMAGING METHOD AND METHOD OF CONTROLLING X-RAY IMAGING APPARATUS

TECHNICAL FIELD

The present invention relates to an imaging apparatus, an imaging method and a method of controlling an imaging apparatus that use X-rays.

BACKGROUND ART

Non-destructive examination methods using X-rays are being popularly employed in various fields extending from industrial fields to medical fields. X-rays are electromagnetic waves having a wavelength within a range of about 0.01 to 100 Å ($10^{-12}$ to $10^{-8}$ m). X-rays having a relatively short wavelength ($\lambda$=0.01 to 1 Å) are referred to as hard X-rays, whereas X-rays having a relatively long wavelength ($\lambda$=1 to 100 Å) are referred to as soft X-rays.

For example, the X-ray absorption contrast method, which utilizes differences in the X-ray absorption capacity, has been finding applications in the field of security check such as examination of internal fissures of steel materials and examination of hand carry baggage to exploit the high transmission power of X-rays.

On the other hand, the technique of X-ray phase contrast imaging, which is based on phase shifts of X-rays, is effective for examining low density objects, although the X-ray absorption contrast method performs only relatively poorly for examining such objects. Thus, the X-ray phase contrast imaging technique is finding applications in the field of imaging of phase separation structures of polymer materials.

Meanwhile, the electron density distribution is required when determining the penetration depth of particles in the body when making a plan for particle beam cancer therapy.

Japanese Patent Application Laid-Open No. 2007-082663 describes a method of computationally determining data for preparing an image of electron density distribution and effective atomic numbers by using X-rays. More specifically, the above-cited patent document describes a method of acquiring data for preparing an image of electron density distribution and effective atomic numbers from an absorption contrast image, utilizing monochromatic X-rays having two or more energies.

DISCLOSURE OF THE INVENTION

However, the method described in Japanese Patent Application Laid-Open No. 2007-082663 is accompanied by a problem that a complex device is required for the method because X-rays having two or more wavelengths must indispensably be employed.

Additionally, since the method described in the above-cited patent document cannot obtain a sufficient contrast for light elements, it can give rise to errors because it only utilizes an absorption contrast image.

In view of the above-identified circumstances, it is therefore an object of the present invention to provide an X-ray imaging apparatus, an X-ray imaging method and a method of controlling such an X-ray imaging apparatus that can simplify the device and computationally determine effective atomic numbers for light elements with small error factors.

According to the present invention, the above object is achieved by providing an X-ray imaging apparatus including: an X-ray generation unit for generating X-rays; a detector for detecting X-rays emitted from the X-ray generation unit and transmitted through an object of examination; a computing unit for computationally determining a quantity of an X-ray phase attributable to the object of examination and an X-ray transmittance of the object of examination from data detected by the detector and further computationally determining an effective atomic number of the object of examination from $\rho_e t$ ($\rho_e$: electron density, t: thickness of the object of examination) determined from the quantity of the X-ray phase and $\mu t$ ($\mu$: linear attenuation coefficient) determined from the X-ray transmittance.

In another aspect of the present invention, there is provided an X-ray imaging method including: a step of detecting X-rays transmitted through an object of examination; and a step of computationally determining a quantity of an X-ray phase attributable to the object of examination and an X-ray transmittance of the object of examination from data detected in the detection step and further computationally determining an effective atomic number of the object of examination from $\rho_e t$ ($\rho_e$: electron density, t: thickness of the object of examination) determined from the quantity of the X-ray phase and $\mu t$ ($\mu$: linear attenuation coefficient) determined from the X-ray transmittance.

Thus, according to the present invention, there are provided an X-ray imaging apparatus, an X-ray imaging method and a method of controlling such an X-ray imaging apparatus that can simplify the device and computationally determine effective atomic numbers with small error factors even for light elements.

Further features of the present invention will become apparent from the following description of exemplary embodiments with reference to the attached drawings.

BRIEF DESCRIPTION OF THE DRAWINGS

FIG. 9 is a process flowchart of the computing unit described in the third embodiment.

BEST MODE FOR CARRYING OUT THE INVENTION

Figure 1:
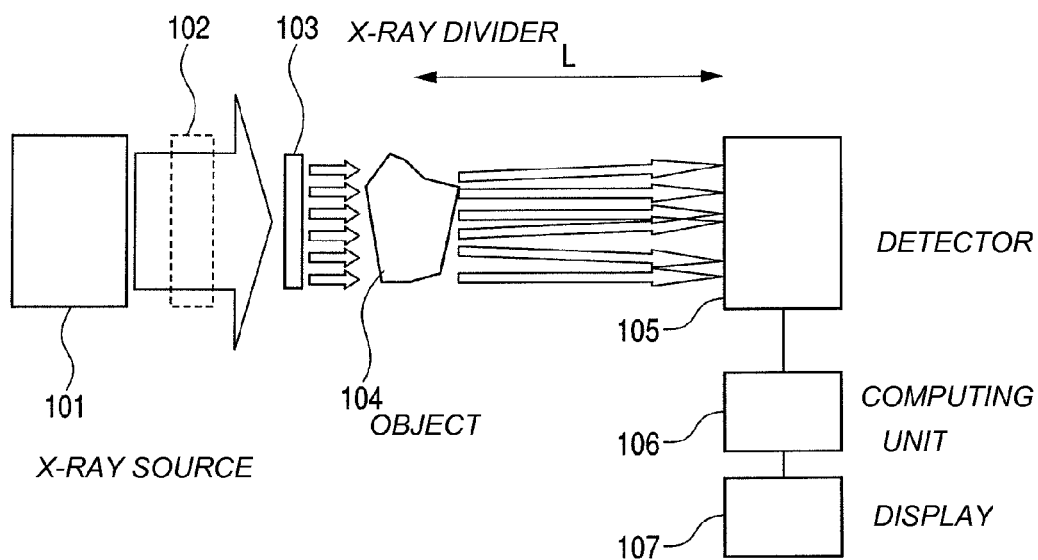
FIG. 1 is a schematic block diagram of the device described in the first embodiment.

Now, the present invention will be described in greater detail by referring to the accompanying drawings that illustrate embodiments of X-ray imaging apparatus and of X-ray imaging method of the invention that can obtain information on effective atomic numbers by utilizing both X-ray absorption and the phase shift of X-rays. The "effective atomic number" is the average atomic number for a substance.

First Embodiment

An imaging apparatus and an image pickup method for acquiring the effective atomic number distribution by utilizing the quantity of X-ray phase and the X-ray transmittance will be described here.

The complex refractive index of X-ray relative to a substance is expressed by formula (1) below:

$$n = 1 - \delta - i\beta \qquad (1)$$

The real part in formula (1) is a term corresponding to phase and the imaginary part is a term corresponding to absorption. For the X-ray absorption of an object of examination, the linear attenuation coefficient μ and the imaginary part β of the complex refractive index of formula (1) can be defined by formula (2) below:

$$\mu t = \frac{4\pi}{\lambda} \int \beta \, dt, \qquad (2)$$

where λ is the X-ray wavelength, which is the effective wavelength when continuous X-rays are used. The symbol t represents the thickness of the object of examination.

When the intensity of transmitted X-rays is observed by means of an X-ray detector and if the intensity of X-rays is $I_o$ in an instance where there is no object of examination present and I in an instance where there is an object of examination present, the relationship of these intensities and the linear attenuation coefficient μ of the object of examination is expressed by formula (3) below:

$$\ln\left(\frac{I_o}{I}\right) = \mu t \qquad (3)$$

The linear attenuation coefficient μ in formula (3) can be expressed by formula (4) below (refer to Daphne F. Jackson and D. J. Hawkes, *Physics Reports* 70, No. 3 (1981) 169-233):

$$\mu = \rho \frac{N_A}{A}(\sigma_{el} + \sigma_{coh} + \sigma_{incoh}, \qquad (4)$$

where ρ is the density of the object of examination, $N_A$ is the Avogadro's number, A is the atomic weight, $\sigma_{el}$ is the photoelectric absorption cross-section, $\sigma_{coh}$ is the coherent scattering cross-section and $\sigma_{incoh}$ is the incoherent scattering cross-section. The photoelectric absorption cross section $\sigma_{el}$ in formula (4) can be expressed by formula (5) below:

$$\sigma_{el} = 4\sqrt{2} Z^5 \alpha^4 \left(\frac{mc^2}{E}\right)^{\frac{7}{2}} \phi_o f, \qquad (5)$$

where Z is the effective atomic number of the object of examination, α is the fine structure constant, E is the X-ray energy, $\phi_0$ is the Thomson scattering cross-section and f is a correction term. The coherent scattering cross-section $\sigma_{coh}$ and the incoherent scattering cross-section $\sigma_{incoh}$ in formula (4) that are put together can be expressed by formula (6) below:

$$\sigma_{coh} + \sigma_{incoh} = Z\Phi_{KN} + (1 - Z^{b-1})\left(\frac{Z}{Z'}\right)^2 \sigma_{coh}(Z', E'), \qquad (6)$$

where $\Phi_{KN}$ is the Klein-Nishina formula and b is a parameter. A value of 0.5 is normally employed for the parameter b as shown in Daphne F. Jackson and D. J. Hawkes, *Physics Reports* 70, No. 3 (1981) 169-233.

Note that $\sigma_{coh}$ (Z', E') is the coherent scattering cross-section of the standard element, Z' is the atomic number of the standard element and E' is the reference energy of the standard element. The reference energy E' of the standard element can be defined by means of formula (7) illustrated below in terms of the atomic number Z' of the standard element, the effective atomic number Z of the object of examination and the X-ray energy E:

$$E' = \left(\frac{Z'}{Z}\right)^{\frac{1}{3}} E \qquad (7)$$

Oxygen is employed as the standard element as shown in Daphne F. Jackson and D. J. Hawkes, *Physics Reports* 70, No. 3 (1981) 169-233.

By rearranging formula (4), and introducing formulas (5) through (7) into formula (4), the linear attenuation coefficient t can be expressed by formula (8) as shown in Y. Ohno, M. Torikoshi, T. Tsunoo, K. Hyodo, *Nuclear Instruments & Methods in Physics Research A* 548 (2005) 72-77:

$$\mu = \rho_e(Z^4 F(Z,E) + G(Z,E)) \qquad (8),$$

where F is a term relating to the photoelectric absorption cross-section and G is a term relating to the scattering cross-section.

As illustrated in formula (8), the linear attenuation coefficient can be interpreted as a function of the electron density $\rho_e$ and the effective atomic number Z of the object of examination. Furthermore, from formula (8), the effective atomic number Z can be expressed by formula (9) below:

$$Z = \left\{ \frac{\frac{\mu}{\rho_e} - G(Z, E)}{F(Z, E)} \right\}^{\frac{1}{4}} \qquad (9)$$

On the other hand, δ, which corresponds to the phase, shows a correlation with the electron density $\rho_e$ as expressed by formula (10) below:

$$\delta = \frac{r_0 \lambda^2}{2\pi} \rho_e, \qquad (10)$$

where $r_0$ is the classical electron radius.

As illustrated by formula (10), the electron density can be computationally determined from information relating to the phase of the X-rays. Additionally, as illustrated by formula (8), both the electron density and the effective atomic number can be computationally determined from information relating to the absorption of X-rays. Thus, the value of $\mu/\rho_e$ can be obtained by obtaining information relating to the phase of the X-rays and information on the absorption of X-rays at the same time by measurement. Then, the effective atomic number and the electron density of the object of examination can be obtained as images by executing a computational process of solving formula (9), using this $\mu/\rho_e$.

FIG. 1 is a schematic block diagram of the device described in the first embodiment, illustrating the configuration thereof. An X-ray dividing element 103, an object of examination 104 and a detector 105 are arranged on the optical path of X-rays emitted from an X-ray source 101, or an X-ray generation unit. X-rays emitted from the X-ray source 101 are spatially divided by the X-ray dividing element 103.

The X-ray dividing element 103 is preferably an element having two-dimensionally arranged holes from the viewpoint of collectively picking up an image of the shift direction and the shift amount of X-rays, although it may alternatively have slit-like apertures. The holes arranged in the X-ray dividing element may not run through the substrate of the element provided that they are of a form that allows X-rays to be transmitted through them. The material of the X-ray dividing element 103 is selected from Pt, Au, Pb, Ta, W and so on that show a high X-ray absorption rate.

X-rays that are spatially divided by the X-ray dividing element 103 are irradiated onto the object of examination 104 and refracted and absorbed by the latter. X-rays whose phase is shifted as a result of refraction are detected by the detector 105 for the position and the intensity thereof. Information on X-rays acquired by the detector 105 is numerically processed by a computation unit 106 and output to a display unit 107, which may typically be a monitor.

The object of examination 104 may be a human body or an inorganic material or an inorganic/organic composite material, if it is not a human body. An object moving mechanism (not illustrated) for moving the object of examination 104 may be additionally provided. An image of a specific spot of the object of examination 104 can be obtained when such an object moving mechanism is provided to appropriately move the object of examination 104.

The detector 105 is selected typically from an X-ray CCD camera, a two-dimensional direct conversion X-ray detector or the like.

When monochromatic X-rays are employed, a monochromatic device such as a monochromator or a multilayer X-ray minor may be arranged between the X-ray source 101 and the X-ray dividing element 103.

Figure 2:
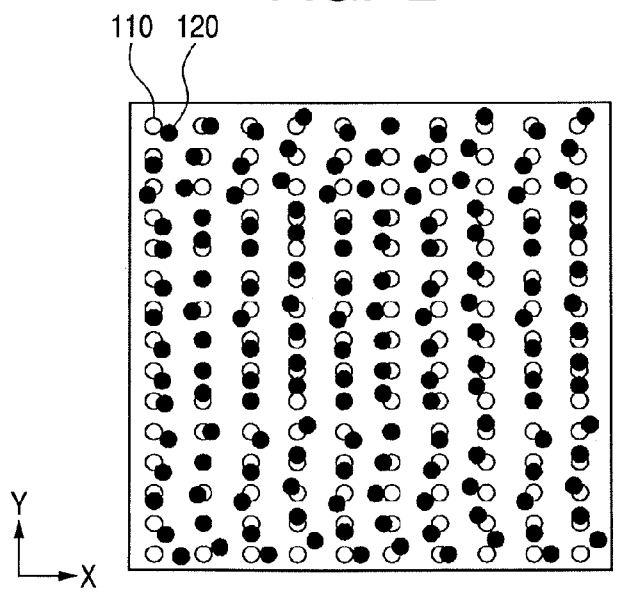
FIG. 2 is a schematic illustration of detected positions that are irradiated by an X-ray.

FIG. 2 is a schematic illustration of a detection image detected by the detector 105. Note that the horizontal direction and the vertical direction of the detection image are defined respectively by an X-axis and a Y-axis.

Detected positions 110 that are indicated by blank circles are of a detection image obtained in a state where there is no object of examination present. The detection image represents the information that is employed as reference when computationally determined the shift amount. On the other hand, the detected positions 120 that are indicated by solid circles are of a detection image observed in a state where there is an object of examination 104 present. The detected positions of each of the two images can be determined from the center of gravity of the intensity distribution of the corresponding one of the X-rays.

Firstly, the detected positions 110 and the detected positions 120 are compared by means of the computing unit 106 to obtain the positional shift amount ($\Delta X$) in the X-direction and the positional shift amount ($\Delta Y$) in the Y-direction. The angles of refraction $\Delta\theta x$ and $\Delta\theta y$ of each refracted X-rays can be obtained by formula (11), using the positional shift amounts ($\Delta X$, $\Delta Y$) the distance L between the object of examination 104 and the detector 105.

The positional shift amount can be computationally determined by storing the detection image observed in a state where there is not any object of examination present in a memory in advance and referring to it at each observation. The distance L may be led out by using the position of the holder of the object of examination 104 as reference. The distance L that is computationally determined by observing a standard substance whose angle of refraction is known and using formula (11) given below may be utilized:

$$\Delta\theta_x = \frac{\Delta X}{L}, \Delta\theta_Y = \frac{\Delta Y}{L} \tag{11}$$

The differential phase contrast image of the object of examination can be obtained by determining the angle of refraction of each X-rays obtained by dividing the original X-rays by means of the X-ray dividing element 103 and using formula (12) illustrated below. Then, the phase $\phi$ of the transmitted X-ray can be reconstructed by integrating the differential phase contrast image.

$$\frac{\partial\phi}{\partial x} = \frac{2\pi}{\lambda}\Delta\theta_x, \frac{\partial\phi}{\partial y} = \frac{2\pi}{\lambda}\Delta\theta_y \tag{12}$$

On the other hand, the phase $\phi$ and $\delta$ have a relationship as defined by formula (13) below:

$$\phi = \frac{2\pi}{\lambda}\delta t, \tag{13}$$

where t is the thickness of the object of examination through which the X-rays are transmitted. In other words, the phase distribution of the transmitted X-rays can be determined from the positional shift of each of the X-rays produced by dividing the original X-rays by means of the X-ray dividing element 103 and formula (14) below can be derived from the formulas (10) and (13):

$$\rho_e t = \frac{1}{r_0\lambda}\phi \tag{14}$$

Figure 3:
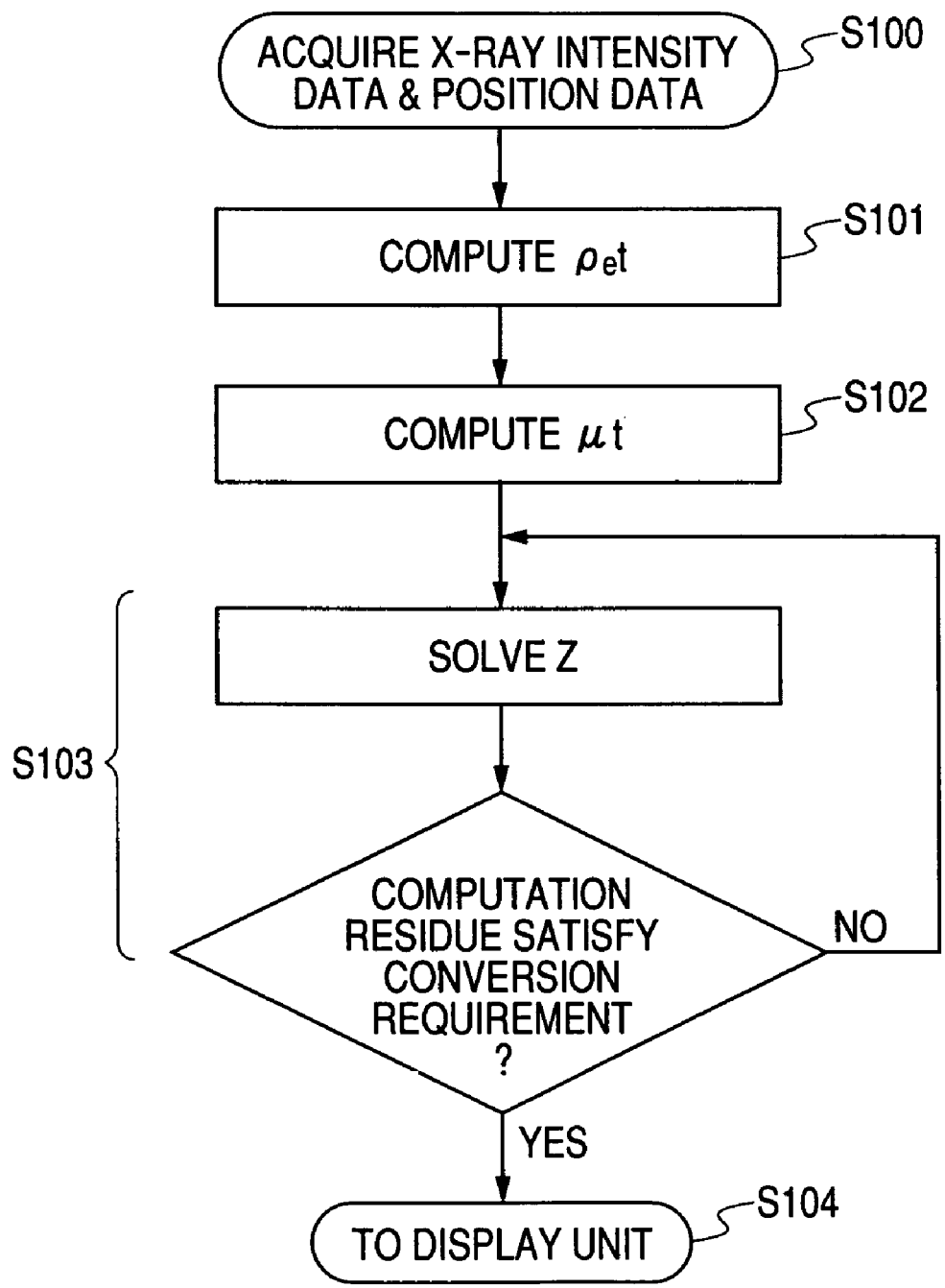
FIG. 3 is a process flowchart of the computing unit described in the first embodiment.

Now, the effective atomic number distribution image reconstruction method adopted by this embodiment will be described below by referring to FIG. 3.

Firstly, X-ray intensity data and position data are acquired from X-rays transmitted through the object of examination (S100).

Since the distance (L) between the object of examination and the X-ray dividing element is known, the angle of refraction ($\Delta\theta$) can be determined from the position data. Additionally, the phase $\phi$ can be determined from the differential phase contrast image obtained by using the angle of refraction. Then, the $\rho_e t$ distribution image of the object of examination can be obtained by using the formula (14) (S101) In other words, the $\rho_e t$ can be determined from the quantity of the X-ray phase.

Then, the $\mu t$ distribution image is determined from the X-ray transmittance of the object of examination by using formula (3) (S102).

Thus, the $\mu/\rho_e$ image can be obtained from the $\rho_e t$ distribution image and the $\mu t$ distribution image. The relationship between $\mu/\rho_e$ and the effective atomic number Z can be expressed by formula (9). It can also be expressed by modifying formula (4) to obtain formula (15) below:

$$\frac{\mu}{\rho_e} = \frac{1}{Z}(\sigma_{el} + \sigma_{coh} + \sigma_{incoh}) \quad (15)$$

In other words, the value of $\mu/\rho_e$ can be computationally determined by giving a provisional effective atomic number Z. The converged value of the effective atomic number Z can be obtained by executing computations repeatedly for matching on the observed value of $\mu/\rho_e$ and the computed value determined from the provisional effective atomic number Z (S103). The repeated computations by means of the computing unit can be terminated by using a reference of determination if the residual of the computations satisfies the conversion requirement or not.

The reconstructed effective atomic number distribution image obtained as information relating to the effective atomic number distribution can be displayed by the display unit 107 (S104). The display unit 107 may display numerical information as information relating to the effective atomic number distribution. Additionally, an X-ray absorption image, an X-ray differential phase contrast image, an X-ray phase contrast image and a $\mu/\rho_e$ image may be displayed. Also, a control means for controlling each of the above-described units and equipment may be provided.

The above description of observation is also applicable when the X-ray dividing element 103 has slit-like apertures and the angle of refraction ($\Delta\theta$) can be determined from the X-ray position data in the direction perpendicular to the extending direction of the slits to determine the phase $\phi$. Alternatively, they may be computationally determined by observing the object of examination, rotating the X-ray dividing element 103 by 90° in the plane of the element to acquire data in the X-direction and those in the Y-direction.

Since this embodiment utilizes the quantity of the phase of X-ray as described above, there can be provided an X-ray imaging apparatus, an X-ray imaging method and a method of controlling such an imaging apparatus that involve error factors only to a small extent relative to light elements. Additionally, the device can be structurally simplified because X-rays of two wavelengths may not necessarily be used.

Second Embodiment

Since the thickness t of the object of examination is unknown, an electron density distribution image cannot be obtained directly by means of the first embodiment if the phase $\phi$ is obtained as indicated by formula (14). A technique of directly obtaining an electron density distribution image on the basis of the principle of computed tomography (CT) will be described in the second embodiment.

Figure 4:
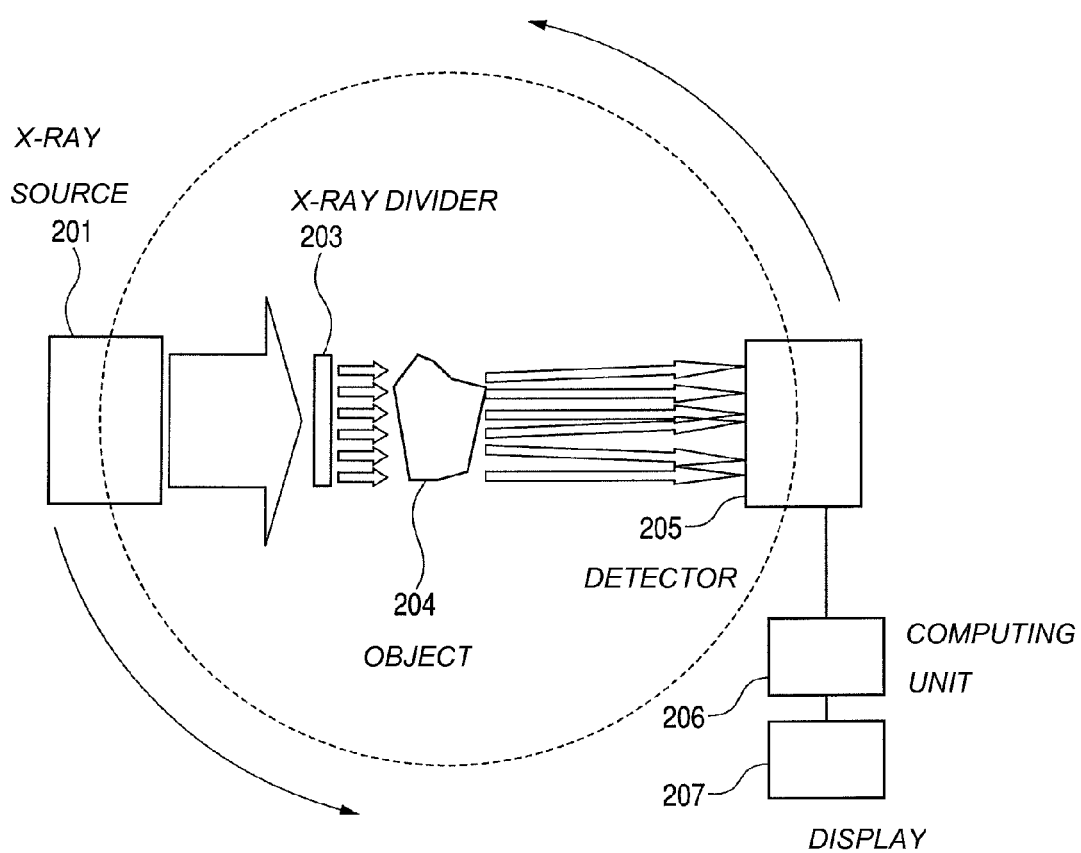
FIG. 4 is a schematic illustration of the CT device described in the second embodiment.

FIG. 4 is a schematic illustration of the CT device described in this embodiment, illustrating the configuration thereof. X-ray source 201, X-ray dividing element 203 and two-dimensional X-ray detector 205 are arranged so as to be synchronously driven to move around an object of examination 204 by a moving mechanism. X-rays that are spatially divided by the X-ray dividing element 203 are irradiated onto the object of examination 204 and transmitted X-rays are detected by the two-dimensional X-ray detector 205. The data obtained by observing parts of the object of examination 204 in this way are processed by computing unit 206 and the computationally determined electron density distribution image is displayed by display unit 207.

Figure 5:
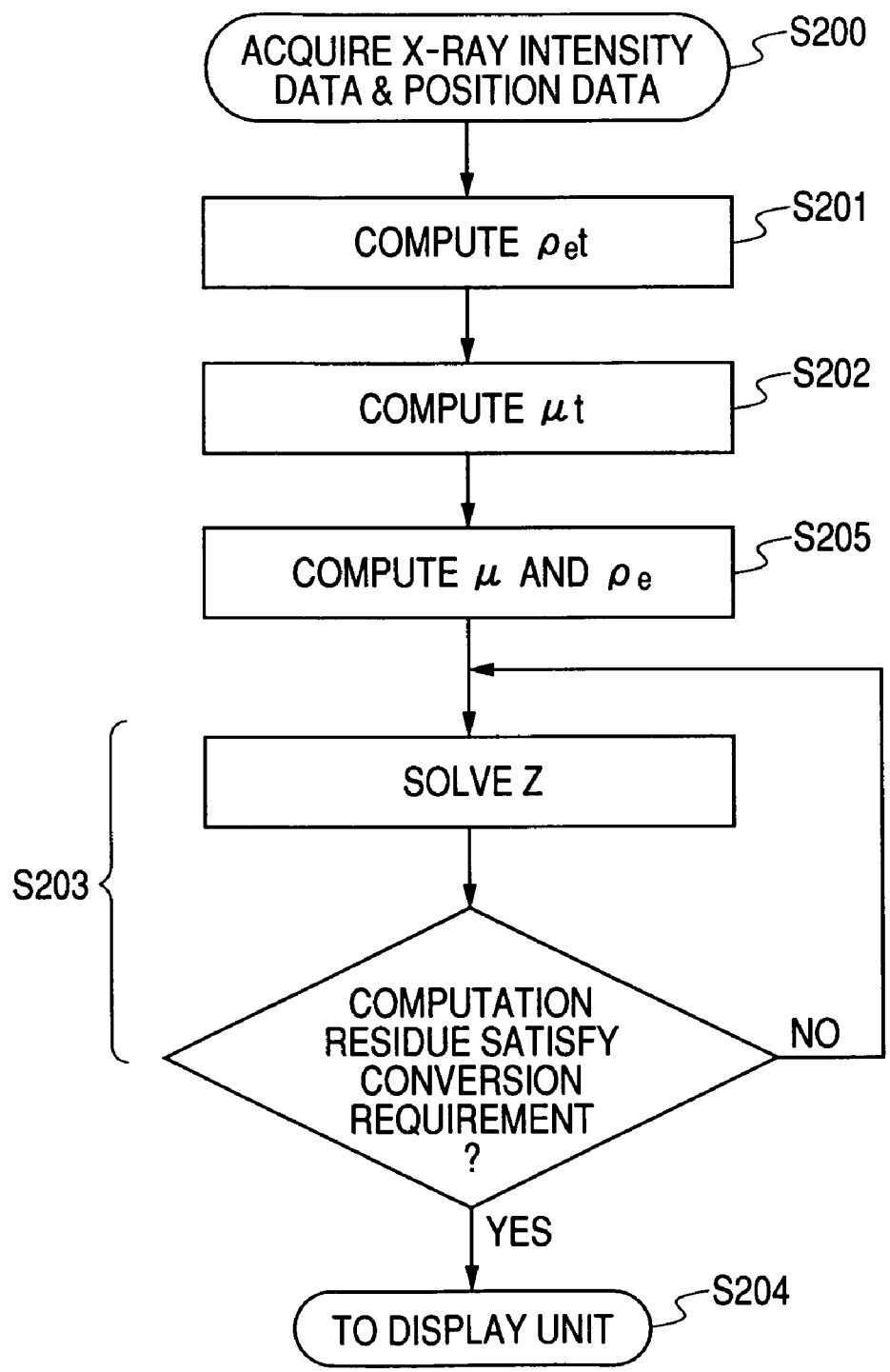
FIG. 5 is a process flowchart of the computing unit described in the second embodiment.

Now, the method of reconstructing the electron density distribution that is adopted by this embodiment will be described by referring to FIG. 5.

Firstly, X-ray intensity data and position data are acquired from X-rays transmitted through the object of examination (S200).

Since the distance (L) between the object of examination and the X-ray dividing element is known, the angle of refraction ($\Delta\theta$) can be determined from the position data. Additionally, the phase $\phi$ can be determined from the differential phase contrast image obtained by using the angle of refraction. Then, the $\rho_e t$ distribution image of the object of examination can be obtained by using formula (14) (S201).

Then, the $\mu t$ distribution image is determined from the change in the intensity of the X-rays transmitted through the object of examination by using formula (3) (S202).

The above processing operation is conducted on all the projection data obtained by the CT device to obtain individual $\rho_e t$ distribution images and $\mu t$ distribution images. Subsequently, tomographic images of $\rho_e$ and $\mu$ are obtained by means of an image reconstruction method (e.g., a filtered back-projection method) that can be used for computed tomography from these distribution images (S205).

Thus, while only the ratio of the linear attenuation coefficient n to the electron density $\rho_e$ can be determined by the first embodiment, a distribution image of the electron density $\rho_e$ and a distribution image of the linear attenuation coefficient $\mu$ can be obtained in Step S205.

Thereafter, an $\mu/\rho_e$ image is computationally determined from the tomographic images of the electron density $\rho_e$ and the linear attenuation coefficient $\mu$ and the converged value of the effective atomic number Z is obtained by a method similar to the one used in the first embodiment (S203).

The repeated computations by means of the computing unit can be terminated by using a reference of determination if the residual of the computations satisfies the conversion requirement or not.

The information on the reconstructed effective atomic number distribution can be displayed by the display unit 107 (S204).

Not only the information on the effective atomic number distribution but also an X-ray absorption image, an X-ray differential phase contrast image, an X-ray phase contrast image, an electron density distribution image, a linear attenuation coefficient distribution image and a $\mu/\rho_e$ image may be displayed on the display unit 107.

Thus, a three-dimensional tomographic image of the effective atomic number and that of the electron density of the object of examination can be obtained in a non-destructive manner as images of physical properties of the object of examination.

Third Embodiment

A technique of acquiring a differential phase contrast image and an absorption image to obtain an effective atomic number distribution that is different from the technique used in the first embodiment will be described in the third embodiment.

Figure 7:
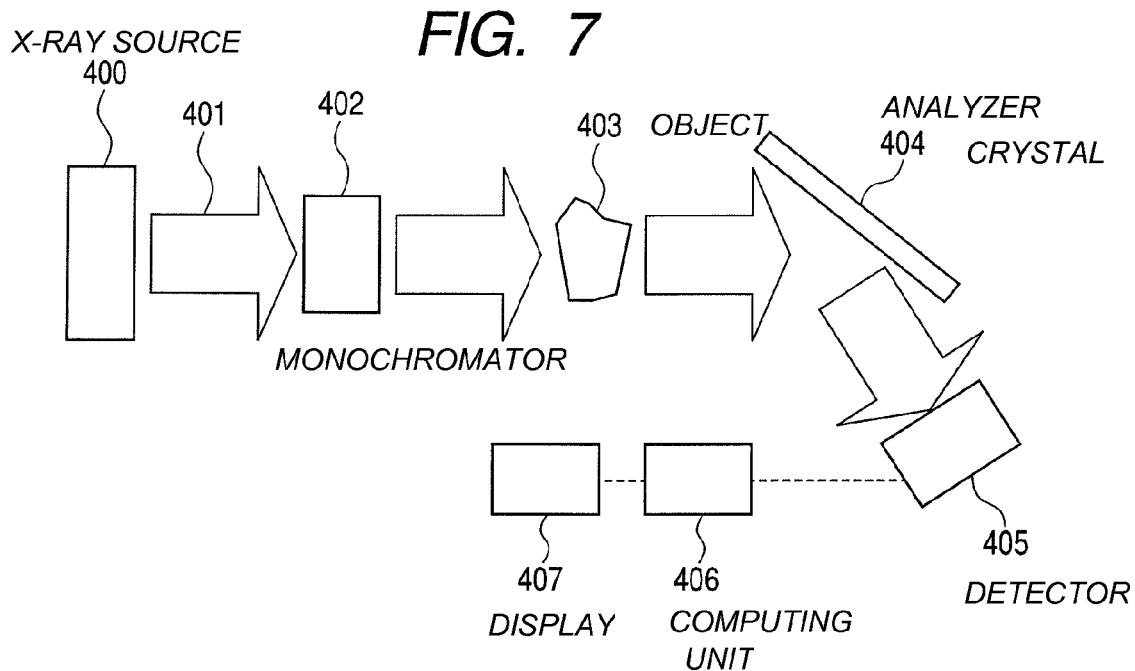
FIG. 7 is a schematic block diagram of the device described in the third embodiment.

FIG. 7 is a schematic block diagram of the device described in this embodiment, illustrating the configuration thereof. White X-rays 401 emitted from X-ray source 400 are monochromatized by monochromator 402 that operates as monochromatic device and enter an object of examination 403. X-rays transmitted through the object of examination 403 are diffracted by an analyzer crystal 404 formed by using a single crystal material such as Si and detected by two-dimensional detector 405.

Figure 8:
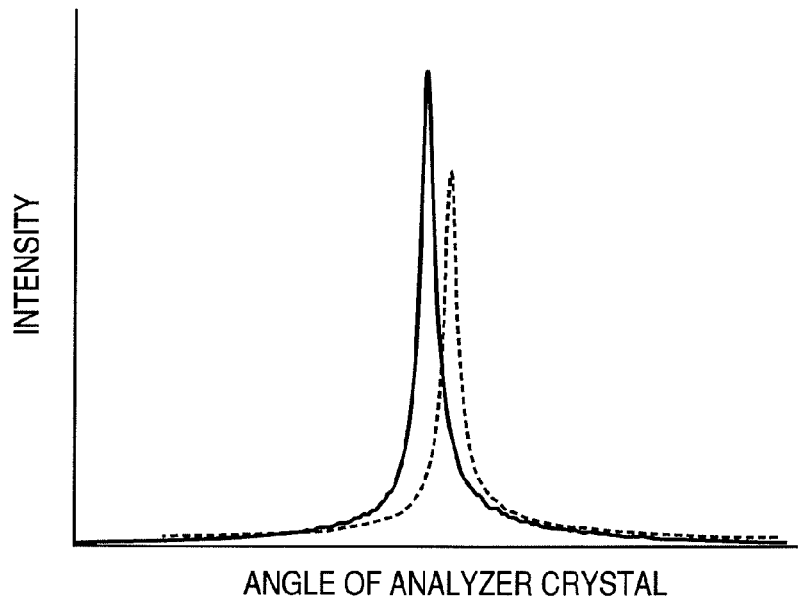
FIG. 8 is an exemplary graph illustrating the X-ray intensity distribution obtained by rotating an analyzer crystal.

The solid line in the graph of FIG. 8 illustrates the intensity distribution (rocking curve) of a pixel of the detector obtained when the analyzer crystal 404 is driven to rotate by an angle that satisfies the X-ray diffraction condition in a state where there is no object of examination 403. In FIG. 8, the horizontal axis indicates the rotation angle of the analyzer crystal 404 and the vertical axis indicates the intensity of X-rays.

On the other hand, the broken line in the graph of FIG. 8 illustrates the rocking curve in a state where there is an object of examination 403.

The angle of incidence of X-rays that strike the analyzer crystal 404 changes due to the refraction effect of the object of examination 403. In other words, there occurs a change of the X-ray intensity spectrum from the solid line to the broken line so that the refraction angle of X-ray can be determined from the shift amount by which the peak position shifts.

The difference of integral intensity between the solid line and the broken line is produced by the X-ray absorption effect of the object of examination 403. Therefore, a differential phase contrast image and an absorption image of the object of examination 403 can be obtained from the peak shift quantity and the change in the integral intensity in a state where there is the object of examination 403 by driving the analyzer crystal to rotate by a very small angle at a time so as to obtain an image thereof. Additionally, a phase contrast image can be obtained by integrating the differential phase contrast image.

A $\rho_e t$ distribution image is computationally determined (S301) from the obtained phase contrast image and then a $\mu t$ image is computationally determined from the absorption image (S302). Then, a $\mu/\rho_e$ image can be obtained from the $\rho_e t$ distribution image and $\mu t$ distribution image. In other words, the $\rho_e t$ and the $\mu t$ are determined from the quantity of the X-ray phase and the X-ray transmittance, respectively.

Additionally, the value of $\mu/\rho_e$ can be computationally determined by giving a provisional effective atomic number Z. The converged value of the effective atomic number Z can be obtained by executing computations repeatedly for matching on the observed value of $\mu/\rho_e$ and the computed value determined from the provisional effective atomic number Z (S303). The effective atomic number distribution image reconstructed in the above-described manner can be displayed by the display unit 407 (S304). Additionally, an X-ray absorption image, an X-ray differential phase contrast image, an X-ray phase contrast image and a $\mu/\rho_e$ image may be displayed.

Example

Figure 6:
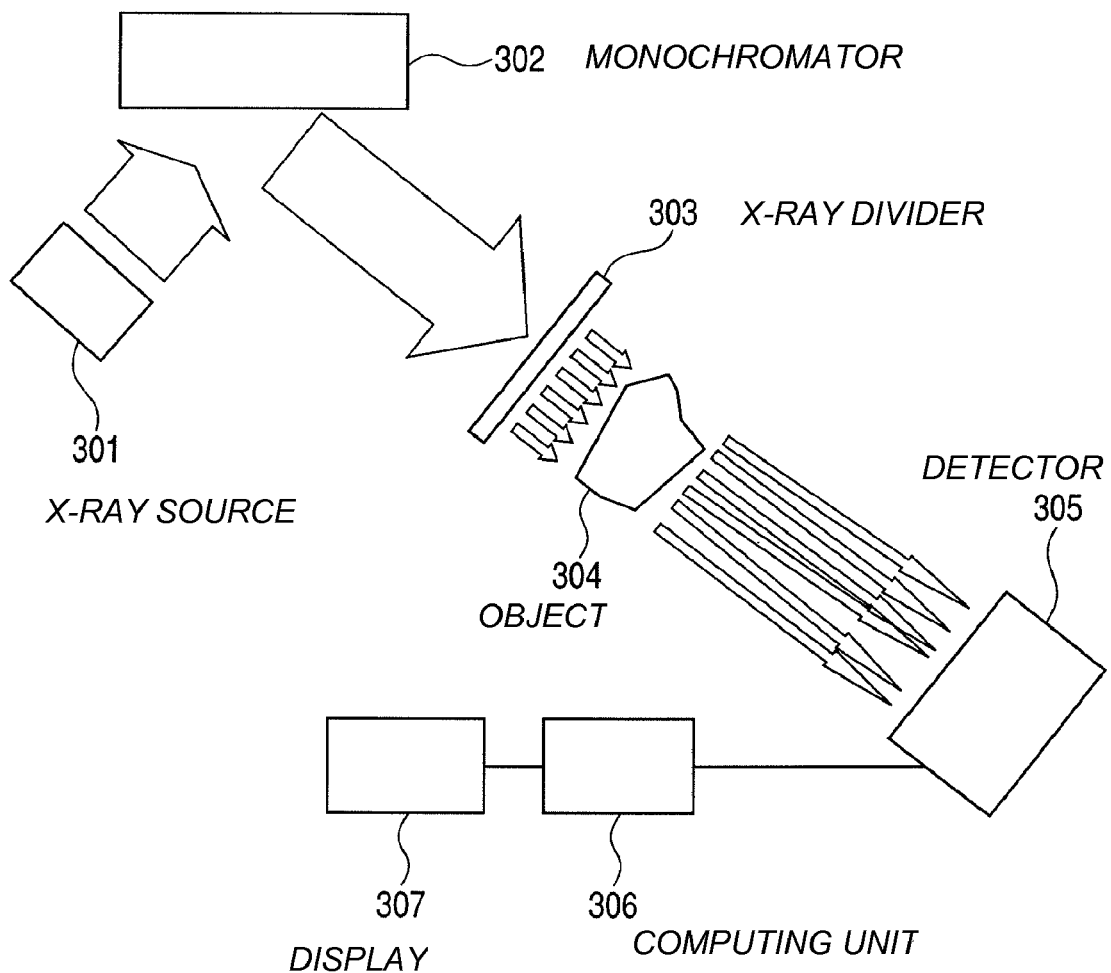
FIG. 6 is a schematic block diagram of the device described in an Example discussed below.

FIG. 6 is a schematic block diagram of the device described in Example, illustrating the configuration thereof.

A rotating-anode-type X-ray generator having a Mo target indicated as X-ray source 301 is employed as X-ray generator. A graphite monochromator or a Ni/C multilayer X-ray mirror are used as X-ray monochromator 302 to extract only characteristic lines of Mo.

X-rays that are monochromatized by monochromator 302 are two-dimensionally divided by X-ray dividing element 303. The X-ray dividing element 303 is formed by cutting a total of 40×20 holes of a diameter of 50 µm through a 100 µm thick Pt plate in 150 µm-pitch, although Pt may be replaced by Au, Pb, Ta, W or some other similar material.

X-rays divided by the X-ray dividing element are irradiated onto object of examination 304. X-rays transmitted through the object of examination 304 are detected by an X-ray detector 305 arranged at a position separated from the object of examination by 2 m for the positions and the intensities of the divided X-rays. The X-ray detector 305 may be an X-ray CCD camera.

The angle of refraction as defined by formula (11) and the value of $\mu t$ as defined by formula (3) are computationally determined by means of computing unit 306 for the position of each of the X-rays on the basis of the position and the intensity of each X-rays observed in a state where there is no object of examination present. Then, the quantity of the differential phase is computationally determined from the angle of refraction by means of formula (12) and a phase contrast image is obtained by integrating the quantity of the differential phase. Furthermore, a $\rho_e t$ distribution image is obtained by means of formula (14) and a $\mu/\rho_e$ distribution image is obtained from the $\rho_e t$ distribution image and the $\mu t$ distribution image. The value of $\mu/\rho_e$ can be computationally determined from formula (9) and formula (15) by giving a provisional effective atomic number Z. As the observed value and the computed value of $\mu/\rho_e$ are obtained, an effective atomic number distribution image can be reconstructed by executing computations repeatedly for matching on them.

The effective atomic number distribution image obtained by means of the computing unit 306 is displayed on a PC monitor that operates as display unit 307. An X-ray absorption image, an X-ray differential phase contrast image, an X-ray phase contrast image and a $\mu/\rho_e$ image may also be displayed on the PC monitor.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-062788, filed Mar. 12, 2008, which is hereby incorporated by reference herein in its entirety.

The invention claimed is:

1. An X-ray imaging apparatus comprising:
   an X-ray generation unit for generating X-rays;
   an X-ray dividing element for spatially dividing X-rays emitted from said X-ray generation unit;
   a detector for detecting X-rays divided by said X-ray dividing element and transmitted through an object of examination; and
   a computing unit for computationally determining an X-ray shift amount attributable to the object of examination and an X-ray transmittance of the object of examination from data detected by said detector and further computationally determining an effective atomic number of the object of examination from $\rho_e t$ ($\rho_e$: electron density, t: thickness of the object of examination) determined from the X-ray shift amount and $\mu t$ ($\mu$: linear attenuation coefficient) determined from the X-ray transmittance.

2. The X-ray imaging apparatus according to claim 1, wherein said computing unit computationally determines the effective atomic number on the basis of $\mu/\rho_e$ computationally determined from the $\rho_e t$ and the $\mu t$.

3. The X-ray imaging apparatus according to claim 1, further comprising:
   a moving mechanism for synchronously moving said X-ray generation unit, said X-ray dividing element and said detector.

4. The X-ray imaging apparatus according to claim 3, wherein said computing unit computationally determines the electron density of the object of examination by way of image reconstruction from the $\rho_e t$.

5. The X-ray imaging apparatus according to claim 4, wherein the image reconstruction is realized by means of a filtered back-projection method.

6. The X-ray imaging apparatus according to claim 1, wherein said computing unit computationally determines a differential phase contrast image of the object of examination, using a positional shift amount obtained by comparing detected positions of X-rays observed in a state where the object of examination is not present and detected positions of X-rays transmitted through the object of examination and a distance between the object of examination and the detector.

7. The X-ray imaging apparatus according to claim 6, wherein said computing unit obtains an X-ray phase contrast image of the object of examination by integrating the differential phase contrast image.

8. The X-ray imaging apparatus according to claim 1, wherein said X-ray dividing element is an element having two-dimensionally arranged holes.

9. The X-ray imaging apparatus according to claim 1, wherein said X-ray dividing element is formed by using a material selected from platinum, gold, lead, tantalum and tungsten.

10. The X-ray imaging apparatus according to claim 1, further comprising:
a display unit for displaying information on the effective atomic number of the object of examination computationally determined by said computing unit.

11. The X-ray imaging apparatus according to claim 1, further comprising:
an object moving mechanism for moving the object of examination.

12. The X-ray imaging apparatus according to claim 1, further comprising:
a monochromator arranged between said X-ray generation unit and said X-ray dividing element to monochromatize X-rays.

13. An X-ray imaging method comprising:
a step of generating X-rays by means of an X-ray generation unit;
a step of spatially dividing the X-rays by means of an X-ray dividing element;
a step of detecting the X-rays divided by the X-ray dividing element and transmitted through an object of examination by means of a detector; and
a step of computationally determining an X-ray shift amount attributable to the object of examination and an X-ray transmittance of the object of examination from data detected by the detector and further computationally determining an effective atomic number of the object of examination from $\rho_e t$ ($\rho_e$: electron density, t: thickness of the object of examination) determined from the X-ray shift amount and $\mu t$ ($\mu$: linear attenuation coefficient) determined from the X-ray transmittance.

14. A method of controlling an X-ray imaging apparatus, comprising:
a step of controlling an X-ray generation unit to generate X-rays;
a step of controlling an X-ray detector to detect the X-rays that were divided by an X-ray dividing element and subsequently transmitted through an object of examination;
a step of controlling a computing unit to computationally determine an X-ray shift amount attributable to the object of examination and an X-ray transmittance of the object of examination; and
a step of computationally determining an effective atomic number of the object of examination from $\rho_e t$ ($\rho_e$: electron density, t: thickness of the object of examination) determined from the X-ray shift amount and $\mu t$ ($\mu$: linear attenuation coefficient) determined from the X-ray transmittance.

15. An X-ray imaging apparatus comprising:
an X-ray generation unit for generating X-rays;
a detector for detecting X-rays emitted from said X-ray generation unit and transmitted through an object of examination;
a computing unit for computationally determining a quantity of an X-ray phase attributable to the object of examination and an X-ray transmittance of the object of examination from data detected by the said detector and further computationally determining an effective atomic number of the object of examination from $\rho_e t$ ($\rho_e$: electron density, t: thickness of the object of examination) determined from the quantity of the X-ray phase and $\mu t$ ($\mu$: linear attenuation coefficient) determined from the X-ray phase transmittance.

16. The X-ray imaging apparatus according to claim 15, further comprising an X-ray dividing element for spatially dividing X-rays emitted from said X-ray generation unit, and obtaining the quantity of the X-ray phase from an X-ray shift amount obtained by using said X-ray dividing element.

17. The X-ray imaging apparatus according to claim 15, further comprising a monochromator for monochromatizing X-rays emitted from said X-ray generation unit and an analyzer crystal arranged between the object of examination and said detector, and obtaining the quantity of the X-ray phase from a refraction angle of X-ray obtained by using said analyzer crystal.

18. An X-ray imaging method comprising:
a step of detecting X-rays transmitted through an object of examination, using an X-ray detector;
a step of computationally determining a quantity of an X-ray phase attributable to the object of examination and an X-ray transmittance of the object of examination from data detected in the detection step; and
a step of computationally determining an effective atomic number of the object of examination from $\rho_e t$ ($\rho_e$: electron density, t: thickness of the object of examination) determined from the quantity of the quantity of the X-ray phase and $\mu t$ ($\mu$: linear attenuation coefficient) determined from the X-ray transmittance,
wherein said steps of computational determination are carried out by means of a computational unit.

19. The X-ray imaging method according to claim 18, wherein the quantity of the X-ray phase attributable to the object of examination is determined from an X-ray shift amount obtained by using an X-ray dividing element for spatially dividing X-rays.

20. The X-ray imaging method according to claim 18, wherein the quantity of the X-ray phase attributable to the object of examination is determined by a refraction angle of X-ray obtained by using an analyzer crystal.

* * * * *